United States Patent [19]
Jones et al.

[11] Patent Number: 5,925,815
[45] Date of Patent: Jul. 20, 1999

[54] METHOD AND DEVICE TO MEASURE FLUID PARAMETERS

[75] Inventors: Terence V. Jones; David R. Buttsworth, both of Oxford, United Kingdom

[73] Assignee: The Secretary of State for Defence in Her Britannic Majesty's Government of the United Kingdom of Great Britain and Northern Ireland, Hants, United Kingdom

[21] Appl. No.: 08/871,683

[22] Filed: Jun. 9, 1997

[30] Foreign Application Priority Data

Jun. 10, 1996 [GB] United Kingdom .................... 9612096

[51] Int. Cl.$^6$ ........................... G01K 13/00; G01N 25/18
[52] U.S. Cl. .............................. 73/25.03; 374/44; 374/164
[58] Field of Search ................................ 73/25.01, 25.03, 73/25.05; 374/35, 40, 39, 43, 44, 41, 101, 107, 142, 143, 164, 179, 185

[56] References Cited

U.S. PATENT DOCUMENTS

| | | | |
|---|---|---|---|
| 2,585,959 | 2/1952 | Minter | 73/25.03 |
| 2,596,992 | 5/1952 | Fleming | 73/25.03 |
| 3,616,677 | 11/1971 | Oppegaard | 73/25.03 |
| 4,080,821 | 3/1978 | Johnston | 73/23.21 |
| 4,183,248 | 1/1980 | West | 374/164 |
| 5,031,126 | 7/1991 | McCulloch et al. | 73/295 X |

*Primary Examiner*—Michael Brock
*Attorney, Agent, or Firm*—Nixon & Vanderhye P.C.

[57] ABSTRACT

A method and device to measure parameters of temperature and gas composition in high temperature fluids which has particular application to compressible unsteady flowing fluid and rapidly changing temperatures of high temperature gases. The device comprises at least two temperature sensing elements, means for pre-setting said elements to different temperatures, and means for determining a parameter of the fluid from temperature readings of said sensing elements taken at least two time instants. The invention also provides a method of measuring fluid temperature by determining differing heat transfer rates from the temperature history of temperature sensors initially set to different temperatures before exposure to the fluid. Based on the same methodology and device, gas composition of binary flows can also be determined.

10 Claims, 2 Drawing Sheets

METHOD AND DEVICE TO MEASURE FLUID PARAMETERS

BACKGROUND OF THE INVENTION

1. Field of the Invention

This invention relates to a method and device to measure fluid parameters of gas composition and temperature. It has particular application for the measurement of rapidly varying temperature in unsteady, compressible fluids, for example gas flowing in gas turbine engine ducts. Another example is the measurement of transient variation in the temperature of a gas which is subject to shock waves.

2. Discussion of Prior Art

Thermocouples are extensively used in many applications to provide accurate and low cost measurement of high temperatures. However their time response is poor due to thermal inertia effects and thus their use in temperature measurement of unsteady or fluctuating flowing fluids is restricted. Other devices, such as thin wire devices, have been used for temperature measurement but these are unsuitable for compressible or unsteady flows since the density, velocity, temperature and pressure of the flow (which are all required to obtain the temperature using these methods) vary independently with time. Optical pyrometry can only be used if optical access to the fluid is possible.

A device for temperature measurement in compressible flow using an aspirating probe has been described by Ng and Epstein in their paper "High Frequency Temperature and Pressure Probe for Unsteady Compressible flows" in Rev. Sci. Inst. Vol.54, No. 12, 1678–1683. This device comprises two constant temperature hot wires located upstream of a choked orifice. By operating the wires at different overheat ratios (probe temperature: flow recovery temperature), it is possible to temporarily resolve both pitot pressure and flow temperature variations in unsteady and fluctuating flow. The successful operation of the probe is dependant on establishing a steady flow in the aspirating channel leading up to and including a choked orifice both of which are parts of the probe itself. Calculation of flow establishment times and experimental measurements suggest that the upper frequency limit for this device is approximately 20 kHz.

SUMMARY OF THE INVENTION

It is an object of this invention to provide a temperature measuring device that is capable of high-frequency measurement of fluid temperature in unsteady and compressible flows.

The invention consists of a device for measuring the temperature of a fluid comprising at least two temperature sensing elements, means for pre-setting said elements to different temperatures, and means for determining the fluid temperature from temperature readings of said elements taken at at least two time instants.

The advantage of using two temperature sensing elements pre-set to different temperatures is that it enables a simple method of determining the temperature of the fluid to be implemented, whereby time-separated temperature measurements from said elements can be used to calculate the fluid temperature; and heat transfer coefficients do not need to be determined. The method eliminates re-calibration of the probe to determine heat transfer coefficients, and allows fluid temperature in flows of arbitrary composition to be measured.

If, as was previously done, just one temperature element is used to find the fluid temperature, the heat transfer coefficient has to be derived in complicated manner from the Nusselt number, which depends inter alia on flow characteristics and probe geometry. It also assumes steady flow with low free-stream turbulence.

This invention relies on the principle that convective heat transfer rate is approximately proportional to the difference between the surface temperature of the temperature sensing element and the temperature of the fluid. If the temperature sensing elements are each initially pre-set to different temperatures, the two different heat transfer rates can be determined by periodically taking measurements of the temperature sensing elements. Determining two heat transfer rates eliminates the need to calculate a heat transfer coefficient. The relationship between the heat transfer rate and the temperature difference is $$q = h(T_f - T_w)$$

where q is heat transfer rate, h is the heat transfer coefficient and $T_f$ and $T_w$ are the temperature of fluid and probe element respectively.

The two measured surface temperatures of the first and second elements $T_{w1}$ and $T_{w2}$ respectively relate to the respective heat fluxes $q_1$ and $q_2$ as follows:

$$q_1 = h(T_f - T_{w1})$$
$$q_2 = h(T_f - T_{w2})$$

From the above equations $$T_f = T_{w1} + q_1(T_{w2} - T_{w1})/(q_1 - q_2)$$

Thus the fluid temperature can be determined from the measured two temperatures and the heat transfer rates $q_1$ and $q_2$. These heat transfer rates can be determined by sampling the temperatures of the temperature sensing elements at short intervals and prior knowledge of the heat diffusion characteristics of the elements, which can be routinely established. It is desirable to calibrate the elements over the whole range of the operating temperatures. Temperature calibrations can be expressed in the usual form (the secondary term may be omitted)

$$R/R_o = 1 + \alpha(T - T_o) + \alpha(T - T_o)^2$$

BRIEF DESCRIPTION OF THE DRAWINGS

By way of example, a number of embodiments of the invention will now be described with reference to the figures of which.

DETAILED DESCRIPTION OF PREFERRED EMBODIMENTS

Figure 1:
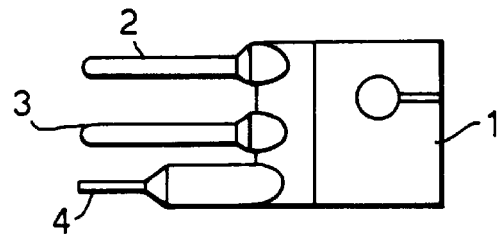
FIG. 1 shows the probe unit for use according to the invention.

FIG. 1 shows the probe unit 1 according to the invention, on its own, which comprises two probes; a "hot" probe 2 and a "cold" probe 3, of similar construction and each having a temperature sensing element located distally (described later with reference to FIG. 2). A pitot probe 4 is incorporated onto the probe unit juxtaposed with the other probes and orientated to point in the direction of flow when the probe unit is inserted into the flow.

Figure 2:
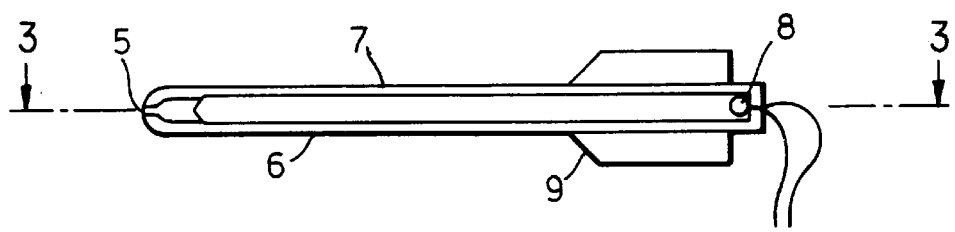
FIG. 2 is a more detailed view of a probe as described with reference to the above figure.

FIG. 2 shows in more detail the design of the probes. Each probe is narrow and cylindrical in its construction and made from quartz 6. At its tip, i.e. distally, it incorporates a temperature sensing element comprising a thin film of platinum 5 painted onto the fused quartz substrate. The probe has a diameter of approximately 3 mm and the thin platinum film has a length of about 1 mm. The platinum film has a thickness of approximately 0.5 $\mu$m and a resistance of 20 $\Omega$. The probes are mounted on macor collars 9 prior to their installation.

Figure 3:
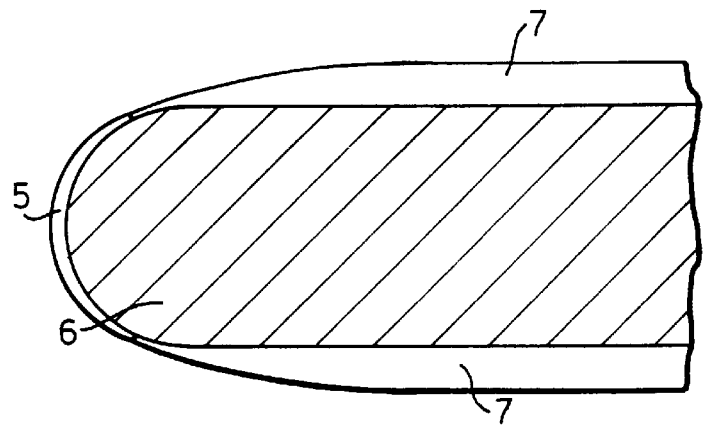
FIG. 3 is a greatly enlarged partial cross section on the line 3—3 0f FIG. 2 and shows the tip of the probe shown in more detail.

FIG. 3 shows in more detail the tip of the probe of FIG. 2 and shows the thin platinum layer 5 on the quartz substrate 6. Electric leads 7 formed by a gold or silver paste are connected to the platinum film, and run to the cool end of the probe These permit the sustained integrity of the solder which joins the electric wire 8 (see FIG. 2) to the probes.

Figure 4:
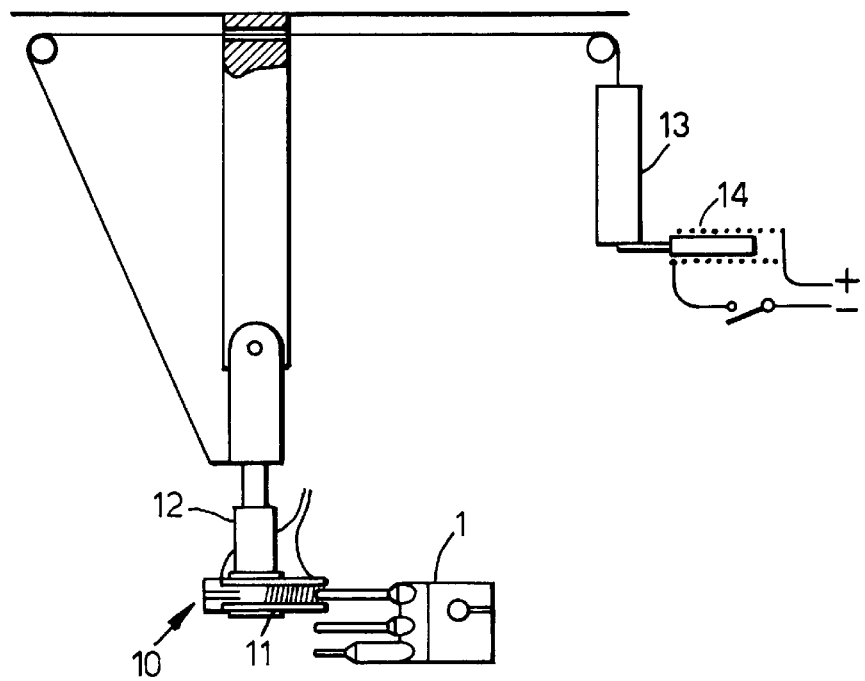
FIG. 4 shows the arrangement of a probe unit for use in accordance with the invention.

FIG. 4 shows the probe unit 1 as described above in operation. In order to generate a difference between the surface temperature of the probes, prior to a temperature measurement run, a pre-heating unit 10 is used to pre-heat one of the probes (hereafter referred to as "the hot probe"). Power from a 7 V source (not shown) is supplied to an aluchrome heating coil 11 incorporated in the pre-heating unit and having a resistance of 2 $\Omega$. Insulation round the heating coil is provided by an oxide ceramic sheath.

In operation for the measurement of rapid temperature changes, before measurements are taken, the hot probe is heated by passing a current through the coil of the pre-heating unit. Immediately before the run, the heating unit, which is mounted on a pivoted member 12, is swung clear of the probes under the action of a weight 13 connected by wire to the member 12, and controllably released by a solenoid latch 14. This causes the pre-heating unit to rotate about the pivot and retract from the hot probe and additionally allows the probe unit to be driven into position or to traverse the fluid flow if required. Temperature readings are taken from both probes at periodic intervals and fed to a suitable data logging device which is connected to a computer so that heat transfer rates and thereby fluid temperature can be calculated from the readings from the temperature sensor elements.

Figure 5:
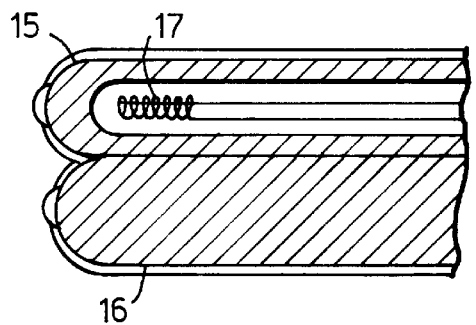
FIG. 5 is a partly cut-away perspective view showing an alternative embodiment of the invention comprising a single probe.

FIG. 5 shows a further embodiment of the invention which comprises a single probe comprising two segments 15,16. Each segment of the probe has an essentially similar construction to the probe described above. The quartz rod of one segment 15 of the probe is hollow and a heating element 17 is located distally therein; i.e. adjacent to the thin platinum film temperature sensing element. Before a temperature measurement run, a current is passed through the heating element so that the temperature sensing element (essentially a heat transfer gauge) is heated to a higher temperature than the temperature sensing element located in the other segment of the probe.

Figure 6:
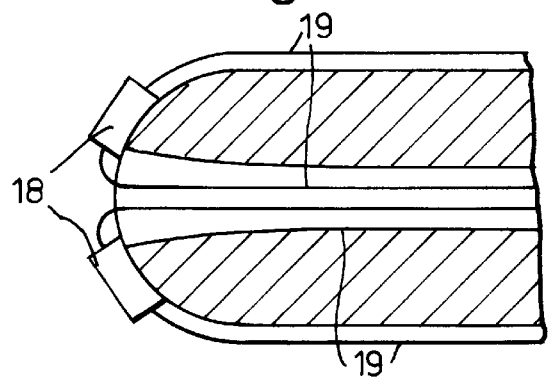
FIG. 6 shows a further embodiment of the invention which eliminates the need for a separate heating element.

FIG. 6 shows an even simpler embodiment of the invention wherein a single probe comprises temperature sensing elements located distally and externally as in the probes described above. The temperature sensing elements 18 are platinum resistance elements as described above. The separate heating element used to pre-heat one of the temperature sensing elements required in the above embodiment is dispensed with. The temperature sensing elements are pre-set to different temperatures prior to a temperature measurement run by passing differing currents through the temperature sensing elements to heat that element to a higher temperature than the other temperature sensing element. Being a resistance temperature sensing element (resistance thermometer) it can act as a heater to heat itself, i.e. the heating element and the temperature sensing element are one and the same. A pair of leads 19 is provided for each element as before.

The temperature probe described also has application in measuring gas composition in binary gas flows. Gas composition measurements are needed, for example, in the analysis of mixing and combusting flows, such as those which occur in scram jet engines. As described above the convective heat transfer coefficient, h is given by:

$$h = (q_1 - q_2)/(T_{w2} - T_{w1})$$

It is possible to establish relationships between the heat transfer coefficient, the Pitot pressure of the gas flow, the geometry of the probe and the gas composition. Therefore if a Pitot tube is provided on the probe then the gas composition can also be determined.

For example, for the case of a hemispherical ended (round-tipped) probe in a hypersonic flow the convective heat transfer coefficient is $$h = C\sqrt{(p_{pit}/r)}$$

where $P_{pit}$ is the Pitot pressure, r is the radius of the probe and C is a strong function of the gas composition but only a weak function of the flow total temperature; gas composition can be determined from C.

For other probe geometries it is prerequisite to formulate a relationship between convective heat transfer coefficient, Pitot pressure and gas composition dependent on the probe geometry.

The concentration probes are essentially identical to the temperature probes described above but also include means to measure Pitot pressure.

We claim:

1. A fluid measurement device comprising:
    at least two temperature sensing elements,
    means for pre-setting said elements to different temperatures, and
    means for determining a parameter of the fluid from temperature readings of said sensing elements taken at at least two time instants
    wherein said temperature sensing elements are located on at least two separate probes
    wherein said means to pre-set said temperature sensing elements comprise a retractable heating unit adapted to receive at least one probe.

2. A device as claimed in claim 1 wherein said temperature sensing elements are resistance thermometers.

3. A device as claimed in claim 2 wherein said temperature sensing elements are thin film heat transfer gauges.

4. A device as claimed in claim 3 wherein said thin film heat transfer gauge includes a thin platinum film.

5. A device as claimed in claim 4 wherein said film is less than 1 $\mu$m thick.

6. A device as claimed in claim 1 wherein said means for pre-setting said temperature sensing elements comprises heating means adapted to heat at least one of said elements.

7. A method of determining the temperature of a fluid comprising the steps of:
   (a) pre-setting at least two temperature sensing elements to different temperatures;
   (b) taking temperature measurements from said elements at least two time instants after exposure to the fluid whose temperature is to be measured; and
   (c) from said measurements calculating the temperature of the fluid wherein $$T_f = T_{w1} + q_1(T_{w2} - T_{w1})/(q_1 - q_2)$$

where $T_f$ is the temperature of the fluid, $T_{w1}$ is the temperature of one element, $T_{w2}$ is the temperature of a second element and $q_1$ and $q_2$ are the heat transfer rates of the first and second elements respectively.

8. A method of determining the concentration of gas in binary gas flows comprising:
   (a) pre-setting at least two temperature sensing elements of a fluid measuring device at different temperatures;
   (b) taking temperature measurements from said elements at at least two time instants when said elements are exposed to the flow;
   (c) from said measurements calculating the convective heat transfer coefficient;
   (d) determining the Pitot pressure in the location of the elements; and
   (e) calculating the gas composition from the convective heat transfer coefficient, the Pitot pressure, and said fluid measuring device.

9. A method of determining in accordance with claim 8 wherein said elements are located on at least one hemispherical probe and wherein step (e) includes calcuating the value of the constant C where $$C = \sqrt{(p_{pit}/r)}$$

where r is the radius of a hemispherical probe used in the determination, and determining the gas composition from C.

10. A fluid measurement device for measuring a parameter of a fluid, said device comprising:
   at least two temperature sensing elements, wherein said temperature sensing elements are located on at least two separate probes
   a retractable heating unit, adapted to receive at least one probe, pre-setting said elements to different temperatures, and
   a computer, responsive to temperature readings of said sensing elements taken at at least two time instants during exposure to said fluid being measured, for determining said parameter of the fluid.

* * * * *